United States Patent
Lee

(10) Patent No.: US 9,026,385 B2
(45) Date of Patent: May 5, 2015

(54) ULTRASOUND SYSTEM AND METHOD FOR PROVIDING DOPPLER SOUND

(75) Inventor: Suk Jin Lee, Seoul (KR)

(73) Assignee: Samsung Medison Co., Ltd., Hongcheon-gun, Gangwon-do (KR)

( * ) Notice: Subject to any disclaimer, the term of this patent is extended or adjusted under 35 U.S.C. 154(b) by 681 days.

(21) Appl. No.: 12/962,258

(22) Filed: Dec. 7, 2010

(65) Prior Publication Data

US 2011/0112778 A1 May 12, 2011

(30) Foreign Application Priority Data

Dec. 11, 2009 (KR) .................. 10-2009-0123003

(51) Int. Cl.
| | |
|---|---|
| *G01F 3/36* | (2006.01) |
| *G06F 3/01* | (2006.01) |
| *G06F 3/02* | (2006.01) |
| *G06F 3/16* | (2006.01) |
| *G01S 15/89* | (2006.01) |
| *G01S 7/52* | (2006.01) |
| *A61B 8/00* | (2006.01) |
| *A61B 8/08* | (2006.01) |

(52) U.S. Cl.
CPC .......... *G01S 15/8979* (2013.01); *G01S 7/52084* (2013.01); *A61B 8/467* (2013.01); *A61B 8/488* (2013.01)

(58) Field of Classification Search
USPC ........... 702/56, 103, 176, 177, 179, 181, 183; 73/661; 600/447
See application file for complete search history.

(56) References Cited

U.S. PATENT DOCUMENTS 5,690,114 A * 11/1997 Chiang et al. .................. 600/447
5,709,209 A * 1/1998 Friemel et al. ................ 600/447

(Continued)

FOREIGN PATENT DOCUMENTS

KR  10-2007-0059260  6/2007
KR  10-2008-0010035  1/2008

(Continued)

OTHER PUBLICATIONS

Korean Office Action issued in Korean Patent Application No. KR 10-2009-0123003 dated Dec. 28, 2011.

(Continued)

*Primary Examiner* — Eliseo Ramos Feliciano
*Assistant Examiner* — Felix Suarez
(74) *Attorney, Agent, or Firm* — McDermott Will & Emery LLP

(57) ABSTRACT

Embodiments for providing Doppler sounds are disclosed. In one embodiment, provided is an ultrasound system which may include: an ultrasound data acquiring unit configured to transmit ultrasound signals to a target object and receive ultrasound echo signals reflected therefrom, to acquire a plurality of ultrasound data associated with the target object, each of which having a synchronization (Sync) number uniquely assigned thereto; a storing unit to store the plurality of ultrasound data therein; an user input unit configured to allow a user to input a user instruction; and a processing unit coupled to the ultrasound data acquiring unit, the storing unit and the user input unit and configured to form a Doppler mode image having the Sync number based on the plurality of ultrasound data, the processing unit being further configured to extract ultrasound data with a Sync number corresponding to the user instruction from the storing unit, thereby forming the Doppler sound based on the extracted ultrasound data.

13 Claims, 5 Drawing Sheets

(56) References Cited

U.S. PATENT DOCUMENTS

| | | |
|---|---|---|
| 6,595,921 B1 | 7/2003 | Urbano et al. |
| 6,780,154 B2 * | 8/2004 | Hunt et al. .................... 600/446 |
| 6,951,541 B2 | 10/2005 | Desmarais |
| 7,223,242 B2 * | 5/2007 | He et al. ........................ 600/454 |
| 7,798,964 B2 * | 9/2010 | Kim et al. ..................... 600/441 |
| 7,984,651 B2 * | 7/2011 | Randall et al. ................. 73/661 |
| 2004/0015079 A1 * | 1/2004 | Berger et al. ................. 600/437 |
| 2004/0147842 A1 | 7/2004 | Desmarais |
| 2007/0016050 A1 * | 1/2007 | Moehring et al. ............ 600/454 |
| 2007/0167763 A1 | 7/2007 | Hyun |
| 2008/0249411 A1 | 10/2008 | Kye et al. |

FOREIGN PATENT DOCUMENTS

| | | |
|---|---|---|
| KR | 10-2008-0090888 | 10/2008 |
| WO | 2007/023438 A2 | 3/2007 |

OTHER PUBLICATIONS

Extended European Search Report issued in European Patent Application No. EP 10193595.5 dated May 29, 2013.

* cited by examiner

ULTRASOUND SYSTEM AND METHOD FOR PROVIDING DOPPLER SOUND

CROSS-REFERENCE TO RELATED APPLICATIONS

The present application claims priority from Korean Patent Application No. 10-2009-0123003 filed on Dec. 11, 2009, the entire subject matters of which is incorporated herein by reference.

TECHNICAL FIELD

The present disclosure relates to an ultrasound system, and more particularly to an ultrasound system for providing Doppler sound.

BACKGROUND

Recently, an ultrasound system has been extensively used in the medical field due to its non-invasive and non-destructive nature. Generally, the ultrasound system has become an important and popular diagnostic tool due to its wide range of applications. Specifically, due to its non-invasive and non-destructive nature, the ultrasound diagnostic system has been extensively used in the medical profession.

In general, such ultrasound system provides a Doppler sound together with a Doppler mode image visualizing velocities of moving objects through the use of a Doppler effect, the Doppler mode image being formed based on Doppler signals obtained in a Doppler mode.

In the related art, there may be a problem in that, when output of the Doppler mode image and the Doppler sound are temporally interrupted halfway, only a previously-outputted Doppler mode image is outputted and the Doppler sound is not outputted. Thus, it is required for an ultrasound system which provides a Doppler sound at a selected timed interval as necessary.

SUMMARY

Embodiments for providing Doppler sound, which corresponds to an area defined on a Doppler mode image, are disclosed herein.

In one embodiment, provided is an ultrasound system which may include an ultrasound data acquiring unit configured to transmit ultrasound signals to a target object and receive ultrasound echo signals reflected therefrom, to acquire a plurality of ultrasound data associated with the target object, each of which having a synchronization (Sync) number uniquely assigned thereto. The ultrasound system may further include a storing unit to store the plurality of ultrasound data therein. The ultrasound system may further include an user input unit configured to allow a user to input a user instruction. The ultrasound system may further include a processing unit coupled to the ultrasound data acquiring unit, the storing unit and the user input unit and configured to form a Doppler mode image having the Sync number based on the plurality of ultrasound data, the processing unit being further configured to extract ultrasound data with a Sync number corresponding to the user instruction from the storing unit, thereby forming the Doppler sound based on the extracted ultrasound data.

In another embodiment, provided is a method of providing a Doppler mode image and Doppler sound in an ultrasound system, which may include transmitting ultrasound signals to a target object and receiving ultrasound echo signals reflected therefrom, thereby acquiring a plurality of ultrasound data associated with the target object, each of which having a synchronization (Sync) number uniquely assigned thereto. The method may further include storing the plurality of ultrasound data in a storage. The method may further include generating the Doppler mode image based on the plurality of ultrasound data. The method may further include allowing a user to input a user instruction. The method may further include extracting ultrasound data with a Sync number corresponding to the user instruction from the storage, to thereby form the Doppler sound based on the extracted ultrasound data.

In yet another embodiment, provided is a computer-readable storage medium storing instructions that, when executed by a computer, cause the computer to perform the operation of transmitting ultrasound signals to a target object and receiving ultrasound echo signals reflected therefrom, thereby acquiring a plurality of ultrasound data associated with the target object, each of which having a synchronization (Sync) number uniquely assigned thereto. The operation may further include storing the plurality of ultrasound data in a storage. The operation may further include generating the Doppler mode image based on the plurality of ultrasound data. The operation may further include allowing a user to input a user instruction. The operation may further include extracting ultrasound data with a Sync number corresponding to the user instruction from the storage, to thereby form the Doppler sound based on the extracted ultrasound data.

The Summary is provided to introduce a selection of concepts in a simplified form that are further described below in the Detailed Description. This Summary is not intended to identify key or essential features of the claimed subject matter, nor is it intended to be used in determining the scope of the claimed subject matter.

DETAILED DESCRIPTION

A detailed description may be provided with reference to the accompanying drawings. One of ordinary skill in the art may realize that the following description is illustrative only and is not in any way limiting. Other embodiments of the present invention may readily suggest themselves to such skilled persons having the benefit of this disclosure.

Figure 1:
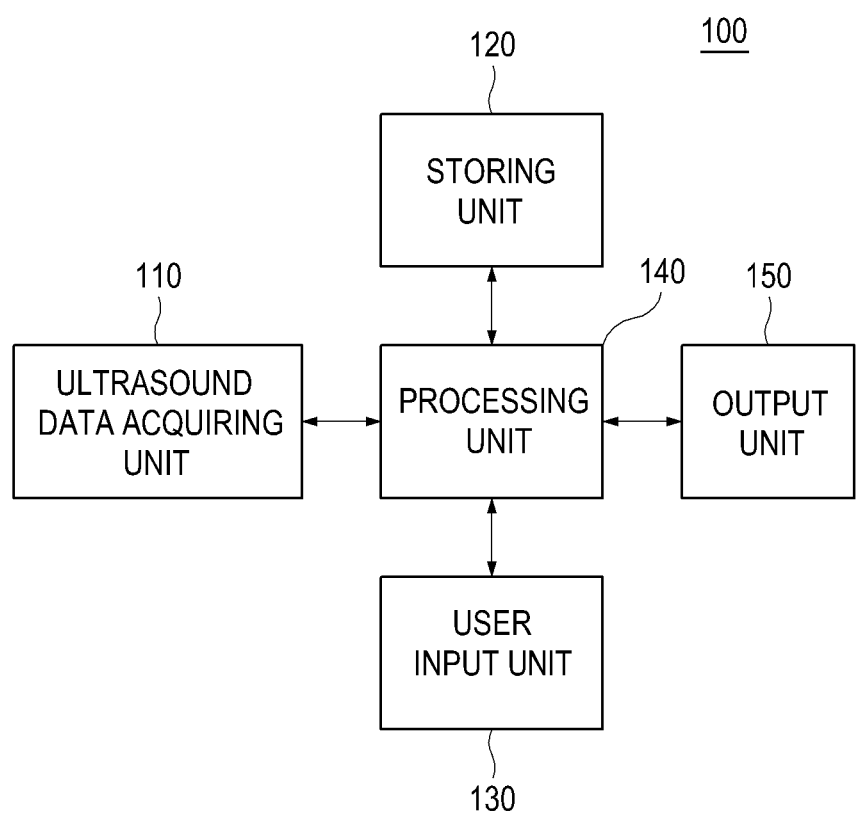
FIG. 1 is a block diagram showing an illustrative embodiment of an ultrasound system.

Referring to FIG. 1, an illustrative embodiment of an ultrasound system 100 is shown.

As depicted therein, the ultrasound system 100 may include an ultrasound data acquiring unit 110. The ultrasound data acquiring unit 110 may be operable to transmit ultrasound signals to a target object and receive signals (i.e., ultrasound echo signals) reflected therefrom. The ultrasound data acquiring unit 110 may acquire ultrasound data based on the received ultrasound echo signals. The acquisition of the ultrasound data will be described in detail by referring to FIG. 2.

Figure 2:
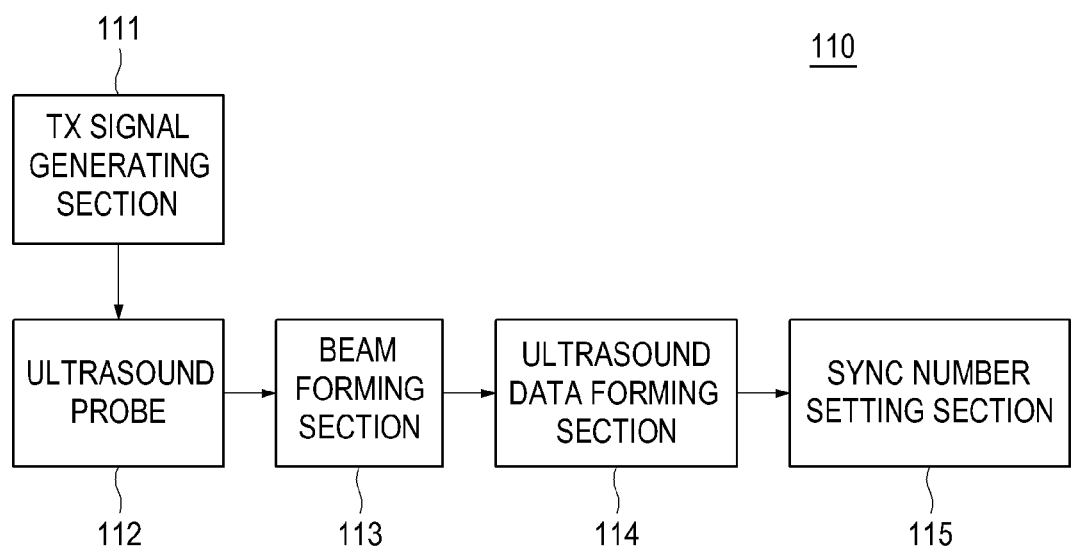
FIG. 2 is a block diagram showing an illustrative embodiment of an ultrasound data acquiring unit shown in FIG. 1.

FIG. 2 is a block diagram showing an illustrative embodiment of the ultrasound data acquiring unit 110 shown in FIG. 1.

As shown in FIG. 2, the ultrasound data acquiring unit 110 may include a transmit (Tx) signal generating section 111. The Tx signal generating section 111 may be operable to generate a plurality of Tx signals in consideration of distances between the transducer elements and focal points. In one embodiment, the Tx signals may be used to obtain a frame of the Doppler mode image. The Tx signal generating section 111 may sequentially and repetitively perform generating the Tx signals, thereby forming the plurality of Tx signals.

The ultrasound data acquiring unit 110 may include an ultrasound probe 112. Upon reception of the Tx signals provided from the Tx signal generating section 111, the ultrasound probe 112 may be operable to convert the received Tx signals into ultrasound signals. The ultrasound probe 112 may be further operable to transmit the so-converted ultrasound signals to the target object and receive ultrasound echo signals reflected therefrom, thereby generating electrical receive (Rx) signals, which are analog signals. The ultrasound probe 112 may sequentially and repetitively perform generating the Rx signals, thereby forming the plurality of Rx signals.

The ultrasound data acquiring unit 110 may further include a beam forming section 113. The beam forming section 113 may be operable to convert the electrical Rx signals provided from the ultrasound probe 112 into digital signals. The beam forming section 113 may be further operable to apply delays to the digital signals in consideration of distances between the transducer elements and focal points, thereby outputting digital receive (Rx)-focused signals. The beam forming section 113 may sequentially and repetitively perform converting and focusing for the Rx signals, thereby forming the plurality of electrical Rx-focused signals.

The ultrasound data acquiring unit 110 may further include an ultrasound data forming section 114. The ultrasound data forming section 114 may be operable to form ultrasound data based on the Rx-focused signals provided from the beam forming section 113. In one embodiment, the ultrasound data may be RF (radio Frequency) data or IQ (In-phase/Quadrature) data. The ultrasound data forming section 114 may sequentially and repetitively perform forming the ultrasound data, thereby forming the plurality of ultrasound data.

The ultrasound data acquiring unit 110 may further include a synchronization (Sync) number setting section 115. The Sync number setting section 115 may be operable to form Sync numbers based on the ultrasound data provided from the ultrasound data forming section 114, and assign the Sync numbers to respective ultrasound data. The Sync number setting section 115 may sequentially and repetitively perform forming and assigning the Sync numbers, thereby forming the plurality of ultrasound data, thereby assigning different Sync numbers to a plurality of ultrasound data.

Referring back to FIG. 1, an illustrative embodiment of the ultrasound system 100 may further include a storing unit 120. The storing unit 120 may store the plurality of ultrasound data provided from the ultrasound data acquiring unit 110, each having a Sync number uniquely assigned thereto. The storing unit 120 may further store a Doppler mode image, a Doppler sound and a sound graph. Below, a detailed description will be made as to the sound graph.

Figure 4:
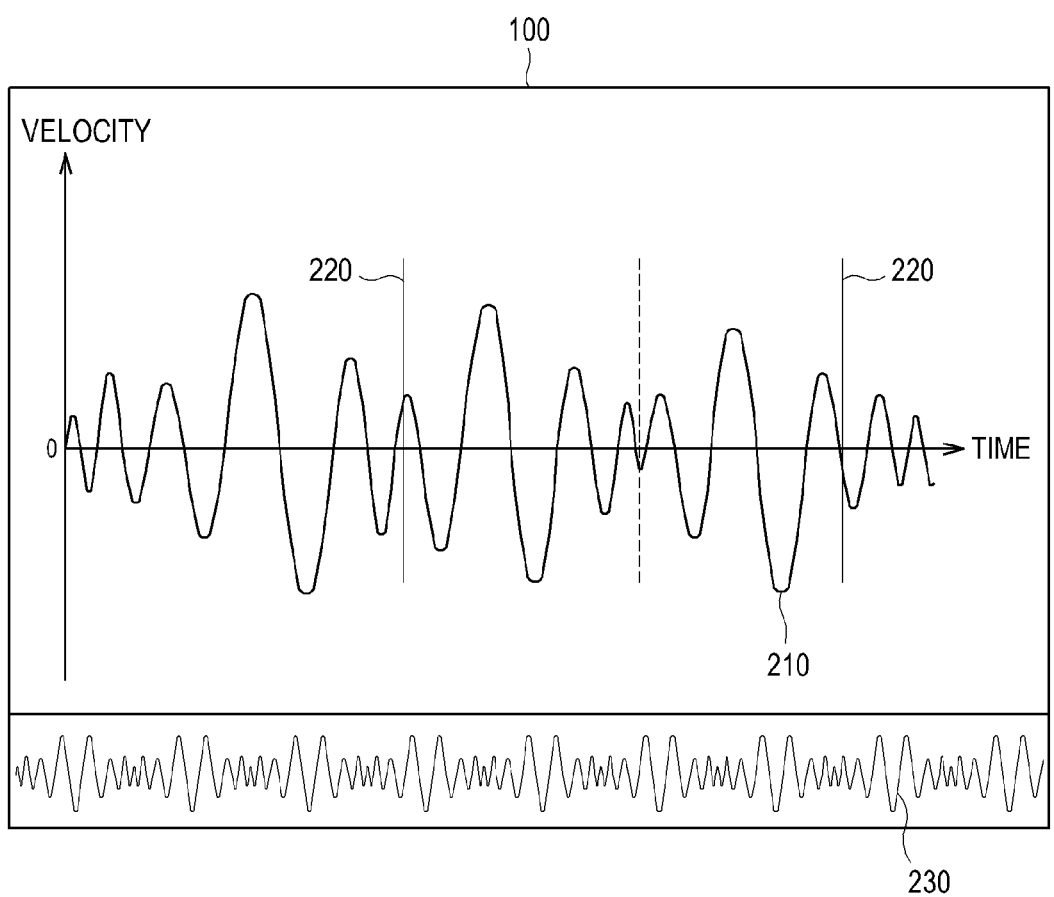
FIG. 4 shows graphs indicative of a region of interest set on a Doppler mode image.

The ultrasound system 100 may further include a user input unit 130. The user input unit 130 may allow a user to input a user instruction. In one embodiment, as shown in FIG. 4, the user instruction may include a first information for setting a region (hereinafter referred to as a "region of interest") 220 whose the Doppler sound is to be formed on a Doppler mode image 210. In FIG. 4, a dotted phantom line represents a position of the Doppler sound currently being outputted. Also in FIG. 4, the Sync number may or may not be displayed. In one embodiment, the user instruction may further include a second information for adjusting a sound field of the Doppler sound. The user input unit 110 may include at least one of a control panel, a mouse, a keyboard, a touch screen and the like.

The ultrasound system 100 may further include a processing unit 140 which is coupled to the ultrasound data acquiring unit 110, the storing unit 120 and the user input unit 130. The processing unit 140 may be operable to form a Doppler mode image based on the ultrasound data provided from the ultrasound data acquiring unit 110. The processing unit 140 may be operable to extract the ultrasound data, which corresponds to the first information provided from the user input unit 130, from the storing unit 120, to thereby form the Doppler sound based on the extracted ultrasound data. The processing unit 140 may be implemented by, for example, CPU (Central Processing Unit), GPU (Graphic Processing Unit) or the like. The operation of the processing unit 140 will be described in detail by referring to FIG. 3.

Figure 3:
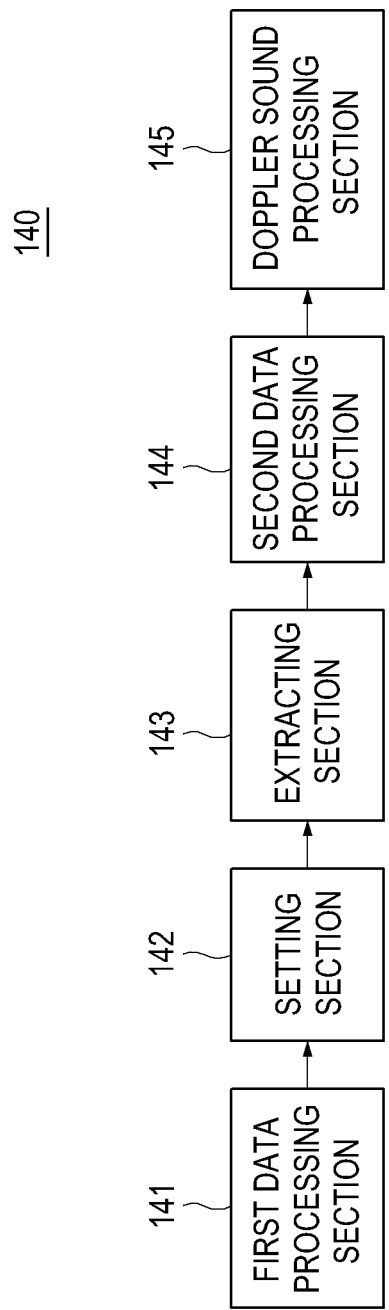
FIG. 3 is a block diagram showing an illustrative embodiment of a processing unit shown in FIG. 1.

FIG. 3 is a block diagram showing an illustrative embodiment of the processing unit 140 shown in FIG. 1.

As shown in FIG. 3, the processing unit 140 may include a first data processing section 141. The first data processing section 141 may be operable to form the Doppler mode image 210 based on the plurality of ultrasound data provided from the ultrasound data acquiring unit 110, as shown in FIG. 4. Wherein, the Doppler mode image 210 may include a Sync number. The Doppler mode image 210 may be stored in the storing unit 120. The first data processing section 141 may be further operable to form the Doppler sound based on the plurality of ultrasound data provided from the ultrasound data acquiring unit 110.

The processing unit 140 may further include a setting section 142. The setting section 142 may be operable to set the region to interest 220 on the Doppler mode image 210 responsive to the first information provided from the user input unit 130, as shown in FIG. 4.

The processing unit 140 may further include an extracting section 143. The extracting section 143 may be operable to detect a Sync number assigned to the Doppler mode image corresponding to the region to interest 220, and scan the storing unit 120, thereby extracting ultrasound data corresponding to the detected Sync number.

The processing unit 140 may further include a second data processing section 144. The second data processing section 144 may be operable to form a Doppler sound based on the ultrasound data extracted at the extracting section 143. The Doppler sound may be stored in the storing unit 120. The second data processing section 144 may be further operable to set on the Doppler mode image 210 a display mark (depicted by a dotted phantom line in FIG. 4) representing a position at which the Doppler sound is currently being outputted. The second data processing section 144 may be further operable to form a sound graph 230 corresponding to the Doppler sound based on the extracted ultrasound data, as shown in FIG. 4. The sound graph 230 may be stored in the storing unit 120.

Figure 5:
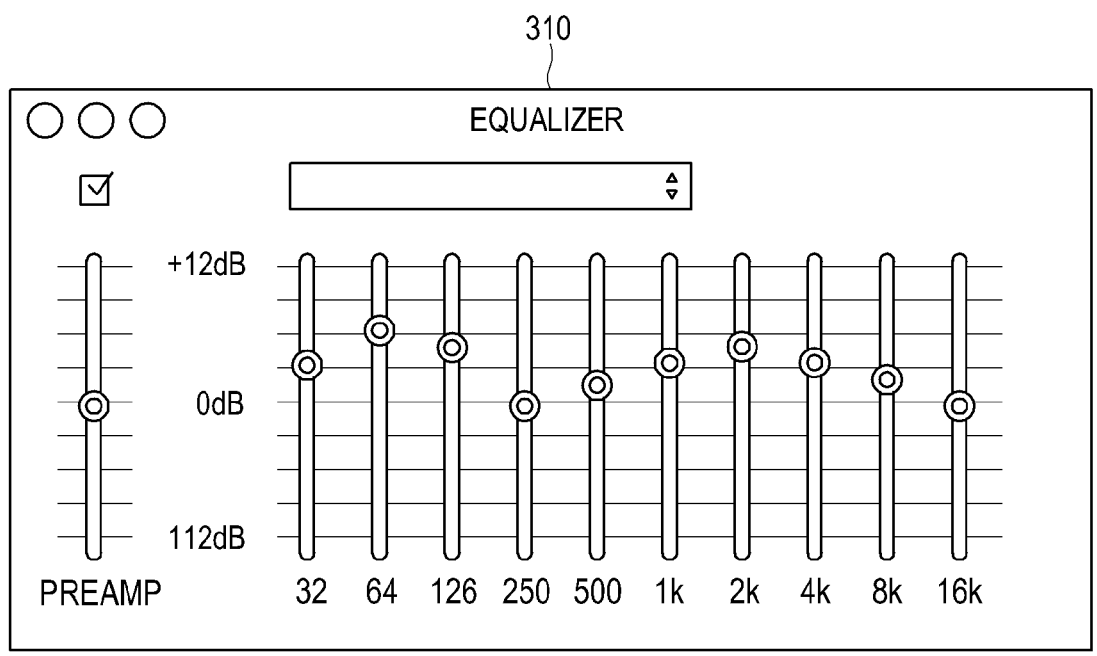
FIG. 5 is an explanatory diagram showing an illustrative embodiment of an open application programming interface.

The processing unit 140 may further include a Doppler sound processing section 145. As shown in FIG. 5, the Doppler sound processing section 145 may be operable to form an open application programming interface (simply referred to as 'open API') 310 for adjusting a sound field of the Doppler sound. The Doppler sound processing section 145 may be further operable to adjust the sound field of the Doppler sound provided from the second data processing section 144 responsive to the second information provided from the user input unit 130. The second information may be stored in the storing unit 120 as a preset parameter.

Referring back to FIG. 1, the output unit 150 may be operable to output the Doppler mode image and the Doppler sound, which are formed in the processing unit 140. In one embodiment, the output unit 150 may further include an image output section (not shown) for outputting the Doppler mode image and a sound output section (not shown) for outputting the Doppler sound.

Therefore, according to the illustrative embodiments of the present disclosure, it is possible to again output a previously-outputted Doppler mode image and further allow a reverse-play function or the like at a timed interval selected by user, thereby enabling the user to minutely diagnose Doppler sounds.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An ultrasound system, comprising:
an ultrasound data acquiring device configured to transmit ultrasound signals to a target object, receive ultrasound echo signals reflected therefrom, thereby acquiring a plurality of ultrasound data, and assign different synchronization (Sync) numbers to the plurality of ultrasound data;
a storage to store the plurality of ultrasound data to each of which a Sync number is uniquely assigned;
a processor coupled to the ultrasound data acquiring device and the storage, and configured to form a Doppler mode image based on the plurality of ultrasound data,
an output device configured to display the Doppler mode image on a screen; and
a user input device configured to receive first information for setting a region on the Doppler mode image, and
wherein the processor being further configured to detect a Sync number assigned to the Doppler mode image corresponding to the region, and extract ultrasound data corresponding to the detected Sync number, and form a Doppler sound corresponding to the region based on the extracted ultrasound data, and
the output device is configured to display the region and output the Doppler sound corresponding to the region.

2. The system of claim 1, wherein the ultrasound data acquiring device includes:
a transmit (Tx) signal generator configured to generate a plurality of Tx signals;
an ultrasound probe, responsive to each of the plurality of Tx signals, configured to transmit the ultrasound signals to the target object and receive the ultrasound echo signals reflected therefrom, thereby generating a plurality of analog receive (Rx) signals;
a beam former configured to perform an analog-to-digital converting and a receive-focusing on each of the plurality of analog Rx signals, thereby forming a plurality of digital receive (Rx)-focused signals;
an ultrasound data former configured to form a plurality of ultrasound data based on the digital Rx-focused signals; and
a synchronization (Sync) number setter configured to assign the unique Sync number to each of the plurality of ultrasound data.

3. The system of claim 1, wherein the processor includes:
a first data processor configured to form the Doppler mode image based on the plurality of ultrasound data;
a setter configured to set the region to interest on the Doppler mode image responsive to the input information;
an extractor configured to detect a Sync number assigned to the Doppler mode image corresponding to the region to interest, and configured to scan the storage to extract ultrasound data corresponding to the detected Sync number; and
a second data processor configured to form the Doppler sound based on the extracted ultrasound data.

4. The system of claim 3, wherein the second data processor is further configured to form a sound graph corresponding to the Doppler sound based on the extracted ultrasound data.

5. The system of claim 3, wherein the processor further includes a Doppler sound processor configured to adjust a sound field of the Doppler sound.

6. The system of claim 1, wherein:
the displayed Doppler mode image includes visualized velocities of a moving object, and
the region of interest is set on the visualized velocities of the displayed Doppler mode.

7. A method of providing a Doppler mode image and Doppler sound in an ultrasound system, the method comprising:
transmitting ultrasound signals to a target object and receiving ultrasound echo signals reflected therefrom, thereby acquiring a plurality of ultrasound data;
assigning different synchronization (Sync) numbers to the plurality of ultrasound data;
storing, in a storage, the plurality of ultrasound data to which a Sync number is uniquely assigned
generating the Doppler mode image based on the plurality of ultrasound data;
displaying the Doppler mode image on a screen;
receiving first information for setting a region on the displayed Doppler image via a user input device;
detecting a Sync number assigned to the Doppler mode image corresponding to the region;
extracting ultrasound data corresponding to the detected Sync number;
forming a Doppler sound corresponding to the region based on the extracted ultrasound data; and
displaying the region and outputting the Doppler sound corresponding to the region.

8. The method of claim 7, wherein the transmitting includes:
generating a plurality of transmit (Tx) signals;
transmitting, responsive to each of the plurality of Tx signals, the ultrasound signals to the target object and receiving the ultrasound echo signals reflected therefrom, thereby forming a plurality of analog receive (Rx) signals;
performing an analog-to-digital converting and a receive-focusing on each of the plurality of Rx signals, thereby forming a plurality of digital receive (Rx)-focused signals;
producing the plurality of ultrasound data based on the plurality of digital Rx-focused signals; and assigning the unique Sync number to each of the plurality of ultrasound data.

9. The method of claim 7, wherein the extracting includes:
setting the region to interest on the Doppler mode image responsive to the input information;
detecting a Sync number assigned to the Doppler mode image corresponding to the region to interest; and
scanning the storage to extract the ultrasound data corresponding to the detected Sync number.

10. The method of claim 7, wherein the forming includes forming a sound graph corresponding to the Doppler sound based on the extracted ultrasound data.

11. The method of claim 7, further comprising adjusting a sound field of the Doppler sound.

12. The method of claim 7, wherein:
the displaying of the Doppler mode image includes displaying the Doppler mode image by visualizing velocities of a moving object, and
the region of interest is set on the visualized velocities of the displayed Doppler mode.

13. A non-transitory computer readable medium encoded with a computer program containing instructions stored therein for causing a computer processor to perform:

transmitting ultrasound signals to a target object and receiving ultrasound echo signals reflected therefrom, thereby acquiring a plurality of ultrasound;
assigning different synchronization (Sync) numbers to the plurality of ultrasound data;
storing, in a storage, the plurality of ultrasound data in which a sync number is uniquely assigned;
generating the Doppler mode image based on the plurality of ultrasound data;
displaying the Doppler mode image on a screen;
receiving first information for setting a region of interest on the displayed Doppler image via a user input device;
detecting a Sync number assigned to the Doppler mode image corresponding to the region;
extracting ultrasound data corresponding to the detected Sync number;
forming a Doppler sound corresponding to the region based on the extracted ultrasound data; and
displaying the region and outputting the Doppler sound corresponding to the region.

* * * * *